(12) United States Patent
De Rezende Neto

(10) Patent No.: US 11,058,415 B2
(45) Date of Patent: Jul. 13, 2021

(54) SUTURE GUIDE AND RELATED PARTS, KITS, AND METHODS

(71) Applicant: UNITY HEALTH TORONTO, Toronto (CA)

(72) Inventor: João Baptista De Rezende Neto, Toronto (CA)

(73) Assignee: UNITY HEALTH TORONTO, Toronto (CA)

( * ) Notice: Subject to any disclaimer, the term of this patent is extended or adjusted under 35 U.S.C. 154(b) by 103 days.

(21) Appl. No.: 16/491,613

(22) PCT Filed: Mar. 8, 2018

(86) PCT No.: PCT/CA2018/050276
§ 371 (c)(1),
(2) Date: Sep. 6, 2019

(87) PCT Pub. No.: WO2018/161169
PCT Pub. Date: Sep. 13, 2018

(65) Prior Publication Data
US 2020/0038013 A1 Feb. 6, 2020

Related U.S. Application Data

(60) Provisional application No. 62/468,582, filed on Mar. 8, 2017.

(51) Int. Cl.
*A61B 17/062* (2006.01)
*A61B 17/04* (2006.01)
(Continued)

(52) U.S. Cl.
CPC ........ *A61B 17/0482* (2013.01); *A61B 17/062* (2013.01); *A61B 17/06066* (2013.01); *A61B 2017/061* (2013.01); *A61B 2017/081* (2013.01)

(58) Field of Classification Search
CPC .......... A61B 17/0482; A61B 17/06066; A61B 17/06; A61B 17/06004; A61B 17/06061;
(Continued)

(56) References Cited

U.S. PATENT DOCUMENTS 3,695,271 A    10/1972  Chodorow
4,147,165 A *   4/1979  Tauschinski ........ A61M 25/065
                                                    604/161
(Continued)

FOREIGN PATENT DOCUMENTS

CN    102512215 A    6/2012
EP     2944268 A1   11/2015

OTHER PUBLICATIONS

International Search Report in PCT/CA2018/050276 (Form PCT/ISA/210).
(Continued)

*Primary Examiner* — Kathleen S Holwerda
*Assistant Examiner* — Lauren Dubose
(74) *Attorney, Agent, or Firm* — ABM Intellectual Property Inc.; Adrienne Bieber McNeil

(57) ABSTRACT

A suture guide includes a first part having a first base piece and a plurality of first needle portions joined to the first base piece. Each first needle portion has a respective first needle portion sidewall. The suture guide further includes a second part having a second base piece and a plurality of second needle portions joined to the second base piece. Each second needle portion has a respective second needle portion sidewall. The first part and second part are moveable between a separated configuration and a joined configuration. In the separated configuration, the first needle portions are spaced away from the second needle portions. In the joined configuration, each one of the first needle portions is positioned
(Continued)

adjacent and cooperates with a respective one of the second needle portions to form a needle.

9 Claims, 13 Drawing Sheets

(51) Int. Cl.
*A61B 17/06* (2006.01)
*A61B 17/08* (2006.01)

(58) Field of Classification Search
CPC ............ A61B 17/0469; A61B 17/0491; A61B 2017/061; A61B 2017/0472; A61M 25/0668; A61M 25/065; A61M 5/3295; A61M 5/3298; A61M 5/34
See application file for complete search history.

(56) References Cited

U.S. PATENT DOCUMENTS

| | | | |
|---|---|---|---|
| 4,316,469 A * | 2/1982 | Kapitanov | ........... A61B 17/068 604/61 |
| 5,507,758 A | 4/1996 | Thomason et al. | |
| 6,120,525 A | 9/2000 | Westcott | |
| 6,730,102 B1 * | 5/2004 | Burdulis, Jr. | ...... A61B 17/0469 606/144 |
| 6,746,456 B2 | 6/2004 | Xiao | |
| 7,318,383 B1 | 1/2008 | Ingram | |
| 8,080,018 B2 | 12/2011 | Kostrzewski | |
| 9,186,134 B2 | 11/2015 | Kostrzewski | |
| 2003/0065336 A1 * | 4/2003 | Xiao | ................. A61B 17/0469 606/144 |
| 2008/0255591 A1 | 10/2008 | Harada et al. | |
| 2011/0301620 A1 | 12/2011 | Betta et al. | |

OTHER PUBLICATIONS

Written Opinion of the International Search Authority in PCT/CA2018/050276 (Form PCT/ISA/237).

Extended European Search Report dated Sep. 30, 2020 in corresponding European Patent Application No. 18763689.9.

* cited by examiner

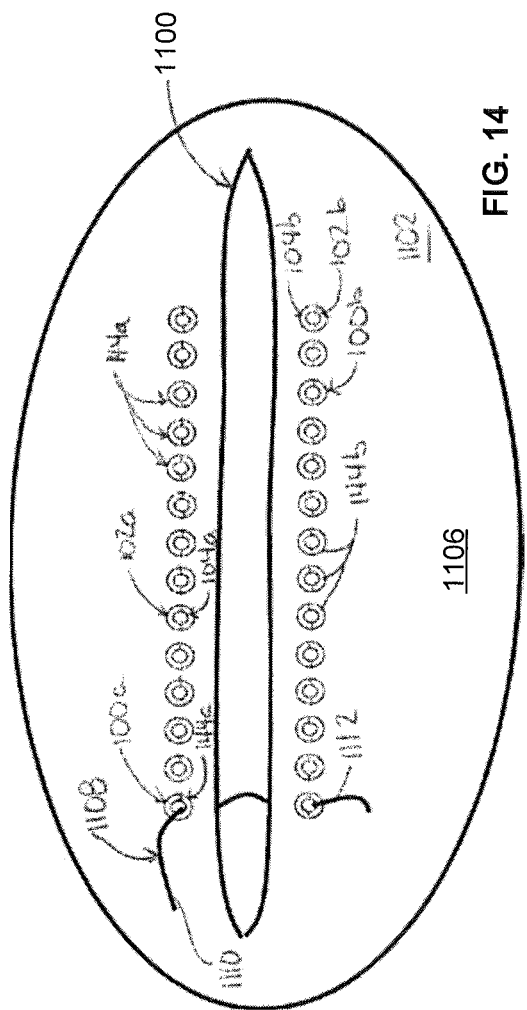
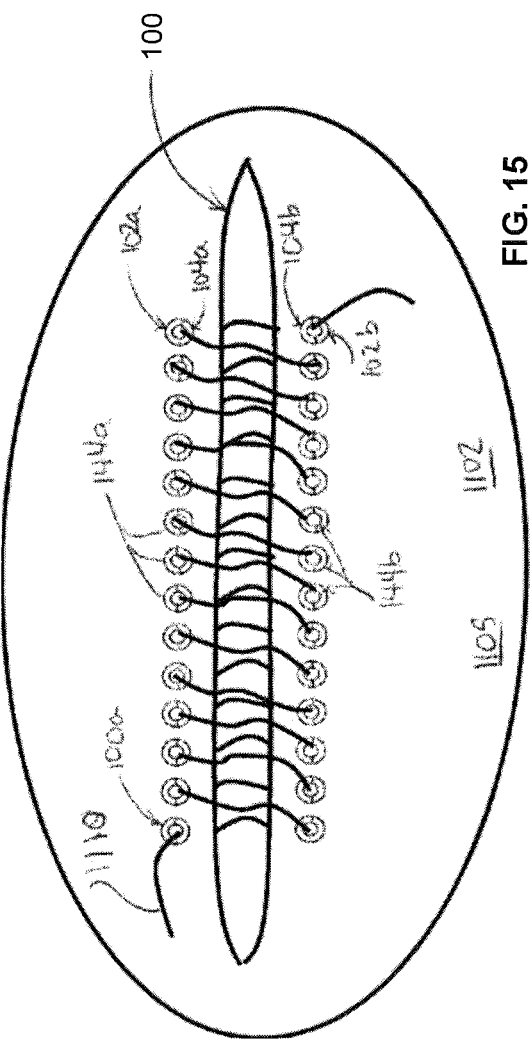
FIG. 14
FIG. 15

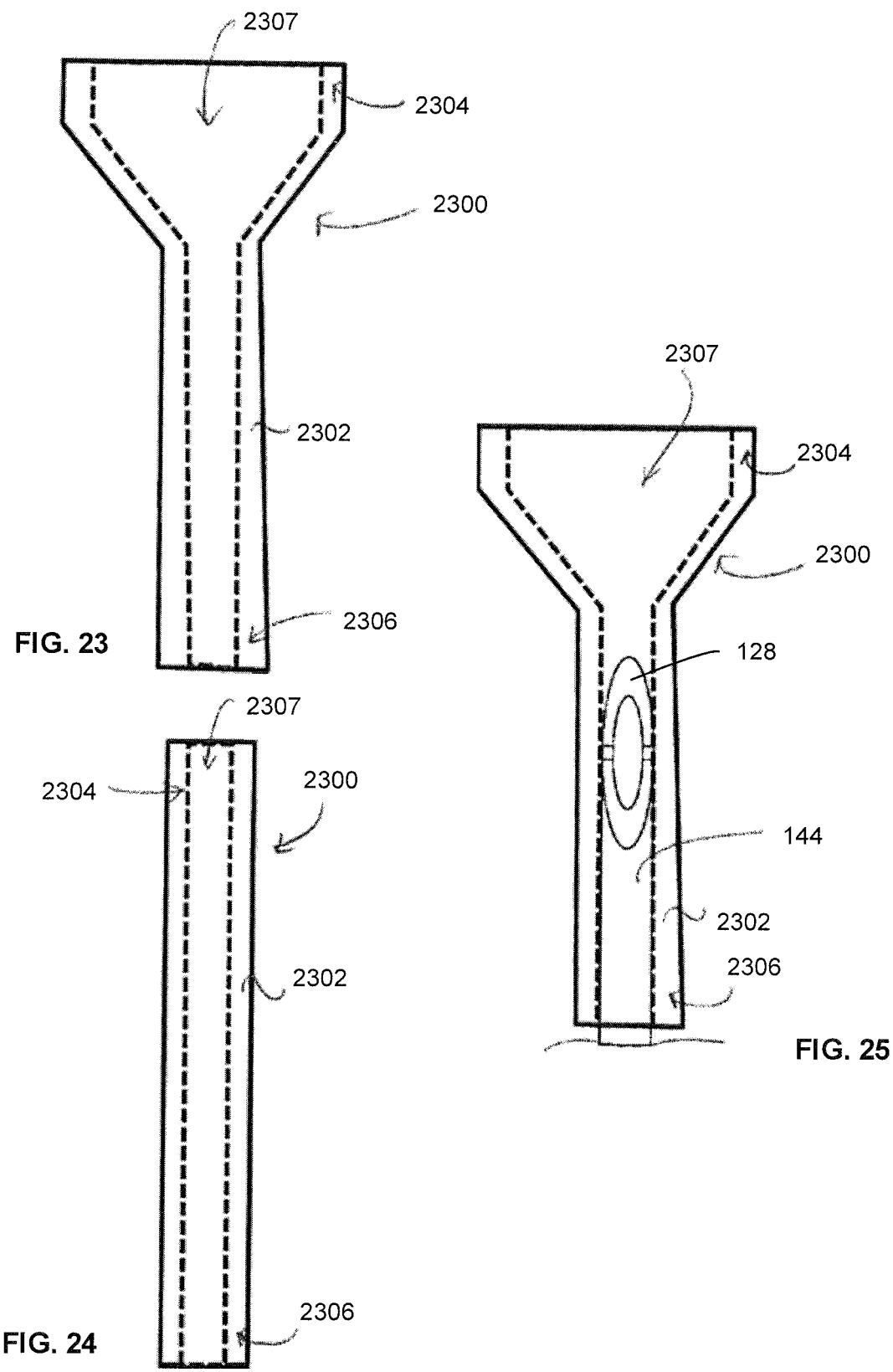

SUTURE GUIDE AND RELATED PARTS, KITS, AND METHODS

CROSS-REFERENCE TO RELATED APPLICATION

This application is a national stage entry of International Patent Application No. PCT/CA2018/050276, which claims the benefit of U.S. Provisional Patent Application No. 62/468,582 filed Mar. 8, 2017; the entire contents of 62/468,582 is hereby incorporated herein in its entirety.

FIELD

This document relates to devices and methods for suturing wounds. More specifically, this document relates to suture guides for facilitating the suturing of a wound, parts for such suture guides, kits containing such suture guides, and methods for suturing wounds.

BACKGROUND

U.S. Pat. No. 9,186,134 (to Kostrzewski) discloses a suturing system for receiving and retaining a suture. The suturing system includes a suture, at least one retainer, and at least one needle. Each needle is able to receive and removably retain the suture within a groove located in a tapered end. The retainer has a body that defines an aperture therethrough. The shape of the aperture is formed by a central passageway, and a pair of diametrically opposed slots extending radially outward from the central passageway. The central passageway is sized to allow passage of the needle therethrough. Each slot defines a tortured path section that permits passage of the suture in a first direction and inhibits passage of the suture in a second direction.

U.S. Pat. No. 4,316,469 (to Kapitanov) discloses a surgical apparatus for suturing soft tissues with lengths of suturing material with spicules. The apparatus comprises at least one hollow needle, mounted in the apparatus body, with a bore to accommodate a length of suturing material, introduced into the tissue to be sutured together with the needle, as well as a stop situated inside the needle bore. The needle is adapted to move longitudinally over the stop so as to retain the length of suturing material in the tissue being sutured while the needle is being withdrawn therefrom, and provided with an actuator to impart the longitudinal movement thereto.

U.S. Pat. No. 6,746,456 (to Xiao) discloses a needle array adapted to deliver sutures for the anastomosis of two separated tissues through the intermediary of suturing and sewing. More particularly, a needle array is provided for delivering sutures for the side-to-side anastomosis of two separated vessels, such as an artery or body lumen and a vessel graft or the like. A method of utilizing a needle array is shown, which will provide sutures for sewing separated tissues together, and especially facilitates the side-to-side anastomosis of body lumens or vessels.

SUMMARY

The following summary is intended to introduce the reader to various aspects of the disclosure, but not to define or delimit any invention.

According to some aspects, a suture guide includes a first suture guide part having a first base piece and a plurality of first needle portions joined to the first base piece. Each first needle portion has a respective first needle portion sidewall. The suture guide further includes a second suture guide part having a second base piece and a plurality of second needle portions joined to the second base piece. Each second needle portion has a respective second needle portion sidewall. The first suture guide part and second suture guide part are moveable between a separated configuration and a joined configuration. In the separated configuration, the first needle portions are spaced away from the second needle portions. In the joined configuration, each one of the first needle portions is positioned adjacent and cooperates with a respective one of the second needle portions to form a needle. Each needle has a respective needle sidewall formed by one of the first needle portion sidewalls and one of the second needle portion sidewalls. Each needle sidewall defines, respectively, a lumen and a pointed tip.

In some examples, each first needle portion sidewall defines a respective first needle portion lumen and has a respective first proximal end joined to the first base piece, and a respective opposed first distal end. In some examples, each second needle portion sidewall defines a respective second needle portion lumen and has a respective second proximal end joined to the second base piece, and a respective opposed second distal end.

In some examples, each first needle portion sidewall defines a respective first opening extending between the first proximal end thereof and the first distal end thereof. In some examples, each second needle portion sidewall defines a respective second opening extending between the second proximal end thereof and the second distal end thereof.

In some examples, when the first suture guide part and the second suture guide part are in the joined configuration, each one of the first needle portion lumens joins with a respective one of the second needle portion lumens to form a respective one of the lumens.

In some examples, the first needle portions are arranged linearly along an edge of the first base piece with each first opening facing away from the first base piece. In some examples, the second needle portions are arranged linearly along an edge of the second base piece with each second opening facing away from the second base piece.

In some examples, the first suture guide part includes a first engagement member, and the second suture guide part includes a second engagement member. The first engagement member may be releasably securable to the second engagement member to maintain the first suture guide part and the second suture guide part in the joined configuration.

In some examples, the first base piece includes a first elongate plate and extends along a first longitudinal axis, and the second base piece includes a second elongate plate and extends along a second longitudinal axis. When the first suture guide part and the second suture guide part are in the joined configuration, the first base piece and second base piece may be positioned side-by-side and the first longitudinal axis and second longitudinal axis may be parallel.

In some examples, the first base piece includes a set of notches therein. The notches can extend transverse to the first longitudinal axis.

In some examples, in transverse section, each first needle portion sidewall and each second needle portion sidewall is semicircular.

In some examples, the suture guide part that is placed distal to a lateral surface of a wound has a base piece with a larger width than the suture guide part that is placed proximal to the lateral surface of the wound during use.

In some examples, the first and second base pieces are made of a material that can be cut using a cutting tool to adjust a length of the base pieces to correspond with a length of a wound to be sutured.

According to some aspects, a suture guide part includes a base piece and a plurality of needle portions joined to the base piece. Each needle portion has a respective needle portion sidewall. Each needle portion sidewall defines a respective needle portion lumen and has a respective proximal end joined to the base piece, and a respective opposed distal end having a pointed tip. Each needle portion sidewall defines an opening extending between the proximal end thereof and the distal end thereof.

In some examples, the needle portions are arranged linearly along an edge of the base piece with each opening facing away from the base piece.

In some examples, the base piece extends along a longitudinal axis. The base piece can include a set of notches therein. The notches can extend transverse to the longitudinal axis.

In some examples, in transverse section, each needle portion sidewall is semicircular According to some aspects, a method for suturing a wound in a tissue includes: a) inserting a first needle through the tissue on a first side of the wound; b) inserting a second needle through the tissue on a second side of the wound; c) passing a first portion of a suture through the tissue on the first side of the wound via a lumen of the first needle; d) passing a second portion of the suture through the tissue on the second side of the wound via a lumen of the second needle; e) removing the first needle from the tissue on the first side of the wound, while maintaining the suture in the tissue on the first side of the wound; f) separating the first needle from the suture; g) removing the second needle from the tissue on the second side of the wound, while maintaining the suture in the tissue on the second side of the wound; and h) separating the second needle from the suture.

In some examples, after step h), the method further includes tightening the suture. In some examples, the method further includes tying the first portion of the suture to the second portion of the suture.

In some examples, the method further includes: i) inserting a third needle through the tissue on the first side of the wound, and j) inserting a fourth needle through the tissue on the second side of the wound.

In some examples, step f) includes separating the first needle into a first needle portion and a second needle portion.

In some examples, step h) includes separating the second needle into a first needle portion and a second needle portion.

According to some aspects, a kit of parts for suturing a wound includes at least one suture guide and a clamp tool. Each suture guide includes suture guide parts each having: i) a base piece and ii) a plurality of needle portions joined to the base piece. Each needle portion has a respective needle portion sidewall. Each needle portion sidewall defines a respective needle portion lumen and has a respective proximal end joined to the base piece and a respective opposed distal end having a pointed tip. Each needle portion sidewall defines a respective opening extending between the proximal end thereof and the distal end thereof. The clamp tool is for pressing the needle portions through a tissue.

In some examples, the clamp tool includes a first arm having a first arm distal end with a first arm end effector, a first arm middle portion, and a first arm proximal end with a first arm grasping member. In some examples, the clamp tool includes a second arm having a second arm distal end with a second arm end effector, a second arm middle portion, and a second arm proximal end with second arm grasping member. The first arm middle portion and second arm middle portion can be rotatably mounted together about a rotation axis, such that movement of the first arm grasping member towards the second arm grasping member effects movement of the first arm end effector towards the second arm end effector.

In some examples, the first arm end effector includes a first abutment surface for abutting the base piece. The first abutment surface can be generally parallel to the rotation axis. In some examples, the second end effector includes a second abutment surface for contacting the tissue. The second abutment surface can be generally parallel to the rotation axis.

In some examples, the first end effector includes a first plate defining the abutment surface. In some examples, the second end effector includes a second plate defining the second abutment surface. The second plate can have an opening extending therethrough for allowing passage of at least some of the needle portions through the second plate during use.

In some examples, the clamp tool comprises a spring coupled to the first and second arms to bias the first and second end effectors in a spaced apart open resting position.

In some examples, the kit of parts further includes at least one needle guard for removable insertion on at least one of the needle portions to protect a user from needle stick injuries when handling the suture guide.

In some examples, the kit of parts further includes a handle attachment for removably engaging at least one suture guide, the handle attachment comprising: a main body, a handle attached to the main body to define a gripping area there between for the user to grip the handle attachment; a base disposed on the main body for receiving the suture guide; and retaining members disposed on the main body for releasably holding the suture guide in place.

In some examples, kit of parts further includes several suture guides having at least one of a different length, and needle portions having a different height.

BRIEF DESCRIPTION OF THE DRAWINGS

The drawings included herewith are for illustrating various examples of articles, methods, and apparatuses of the present specification and are not intended to limit the scope of what is taught in any way. In the drawings:

FIG. 14 is a schematic top view similar to that of FIG. 13, showing a single interrupted stich in laced between the suture guides;

FIG. 15 is a schematic top view similar to that of FIG. 13, showing a continuous laced between the suture guides;

FIG. 23 is a front view of an example needle guard;

FIG. 24 is a side view of the needle guard of FIG. 23;

FIG. 25 is a front view similar to that of FIG. 23, showing a needle of a suture guide positioned inside the needle guard;

DETAILED DESCRIPTION

Figure 1:
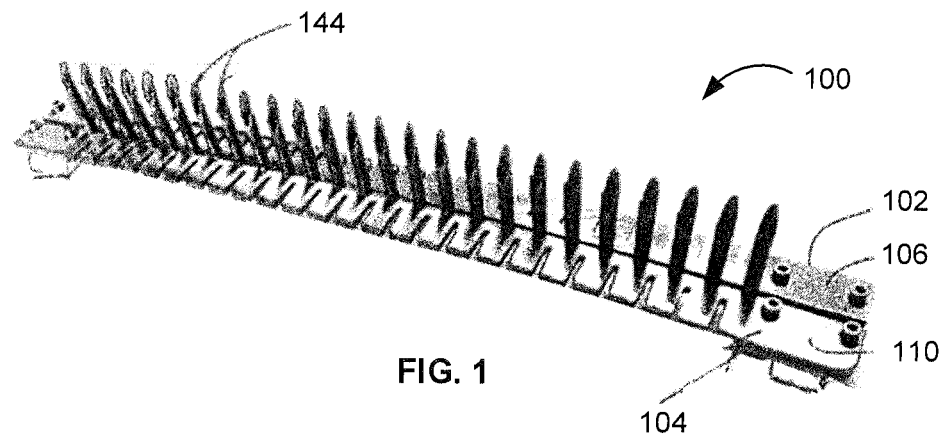
FIG. 1 is a perspective view of an example suture guide, wherein first and second parts of the suture guide are in a joined configuration.

Various apparatuses or processes will be described below to provide an example of an embodiment of the claimed subject matter. No embodiment described below limits any claim and any claim may cover processes or apparatuses that differ from those described below. The claims are not limited to apparatuses or processes having all of the features of any one apparatus or process described below or to features common to multiple or all of the apparatuses described below. It is possible that an apparatus or process described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should also be noted that terms of degree such as "substantially", "about" and "approximately" as used herein mean a reasonable amount of deviation of the modified term such that the end result is not significantly changed. These terms of degree should be construed as including a deviation of the modified term such as 1%, 2%, 5% or 10%, for example, if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made, such as up to 1%, 2%, 5% or 10%, if the end result is not significantly changed.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

Disclosed herein are devices, and related kits, parts, and methods, that may facilitate the suturing of a wound. The wound may be, for example, a laceration (e.g. a wound caused accidentally by trauma) or an incision (e.g. a wound purposefully made by a surgeon such as due to an incision made during surgery). The wound may be in various body parts, including but not limited to the torso, the limbs, or the head. In some specific examples, the wound may be an abdominal wound, and may be a result of abdominal surgery. The wound may be through various tissues, including but not limited to the skin, the subcutaneous tissue, or combinations thereof. The devices described herein may allow for relatively rapid suturing. For example, the devices may allow for a row of punctures to be simultaneously made in the tissue, and for a suture to be threaded through the punctures with relative ease. Furthermore, the devices may allow for the punctures to be relatively accurately and optimally placed. For example, it has been suggested that wound healing can be facilitated when sutures are placed approximately 5 mm from the wound. The devices described herein may guide the placement of the sutures at about this distance.

Figure 3:
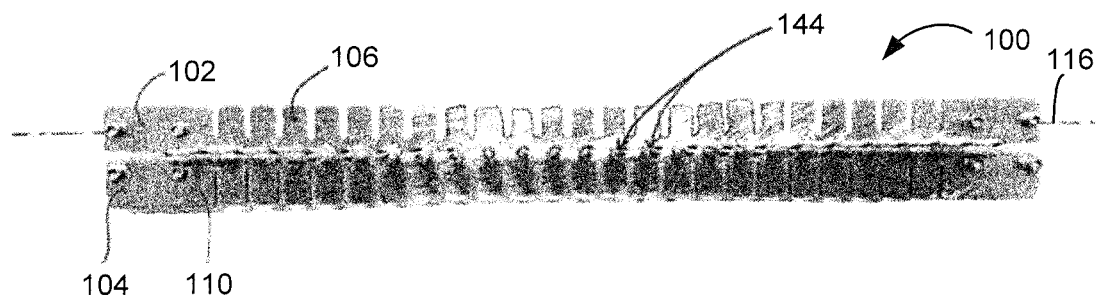
FIG. 3 is a top view of the suture guide of FIG. 1.
Figure 4:
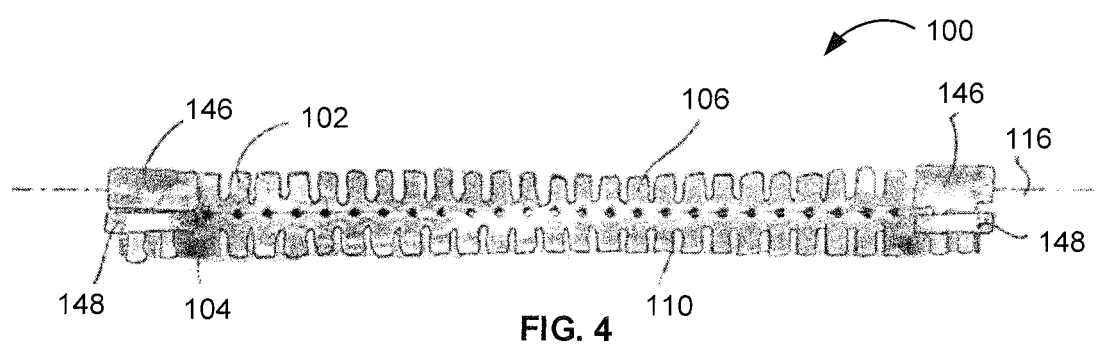
FIG. 4 is a bottom view of the suture guide of FIG. 1.
Figure 5A:
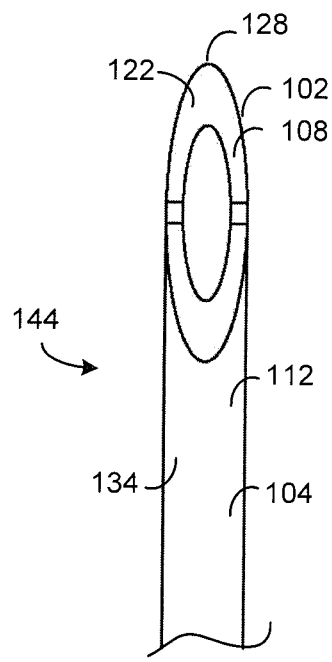
FIG. 5A is an enlarged front view of one of the needles of the suture guide of FIG. 1.
Figure 5B:
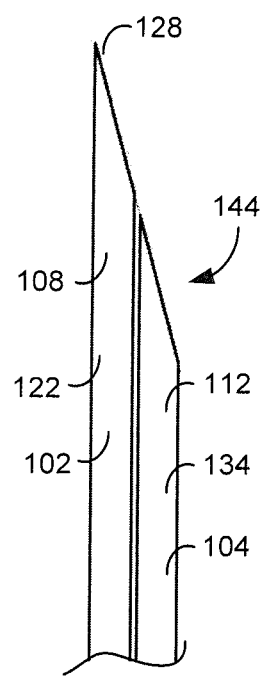
FIG. 5B is a side view of the needle of FIG. 5A.
Figure 5C:
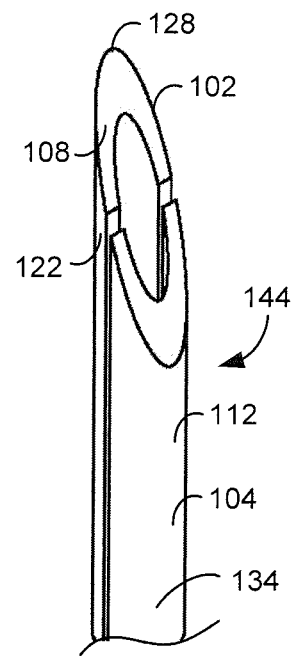
FIG. 5C is a perspective view of the needle of FIG. 5A.
Figure 6:
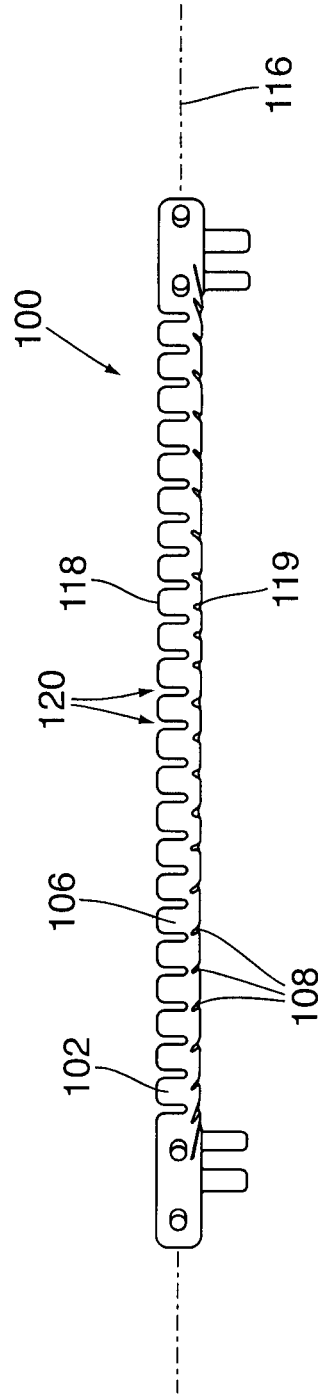
FIG. 6 is a top view of the suture guide of FIG. 1, wherein first and second parts of the suture guide are in a separated configuration.
Figure 9:
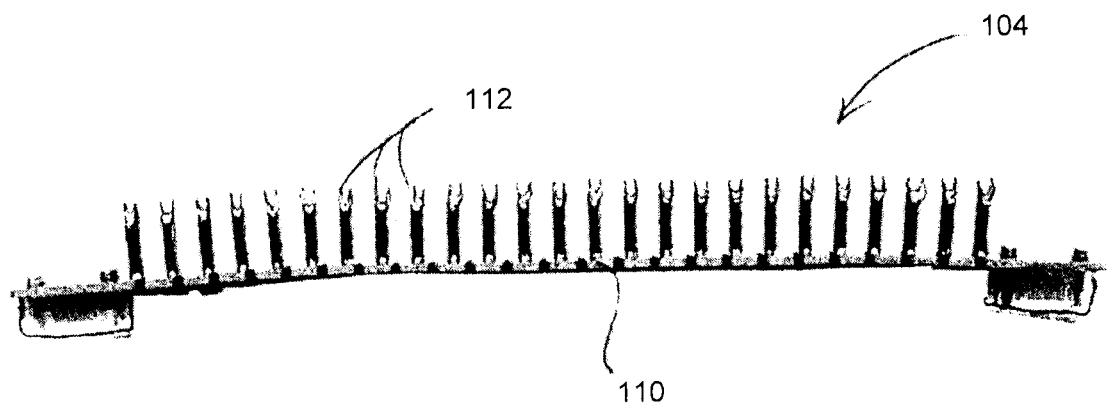
FIG. 9 is a side view of the second part of the suture guide of FIG. 6.
Figure 10A:
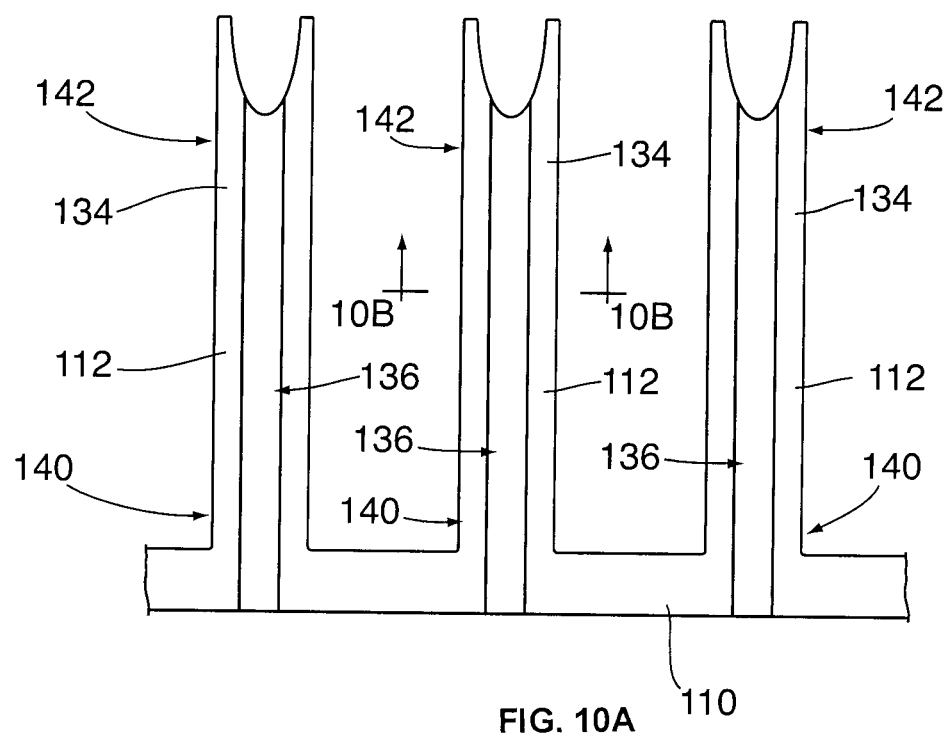
FIG. 10A is an enlarged side view of some of the needle portions of the second part of FIG. 9.
Figure 10B:
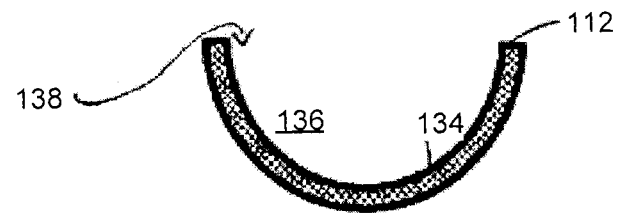
FIG. 10B is a cross section taken along line 10B-10B in FIG. 10A.

Referring now to FIGS. 1 to 4 and 6, an example suture guide 100 is shown, with the needles thereof shown in detail in FIG. 5. In the example shown, the suture guide 100 includes a first suture guide part 102 (also referred to as 'first part 102') and a second suture guide part 104 (also referred to as 'second part 104'). In FIGS. 1 to 5C, the first suture guide part 102 and second suture guide part 104 are in a joined configuration, described in further detail below. In FIG. 6, the first suture guide part 102 and second suture guide part 104 are in a separated configuration, described in further detail below Referring to FIGS. 7 to 8B, the first part 102 is shown in greater detail. In the example shown, the first part 102 includes a base piece 106, and a plurality of needle portions 108 joined to the base piece. Referring to FIGS. 9 to 10B, the second part 104 is shown in greater detail. Similarly to the first part 102, the second part 104 includes a base piece 110 and a plurality of needle portions 112 joined to the base piece 110. In this document, features of the first part 102 may in certain instances be referred to with the prefix 'first', and features of the second part 104 may in certain instances be referred to with the prefix 'second'. For example, the base piece 106 of the first part 102 may be referred to as a 'first base piece 106', and the base piece 110 of the second part 104 may be referred to as 'a second base piece 110'

Referring back to FIGS. 6 to 8B, in the example shown, the first base piece 106 is in the form of a generally elongate and rectangular plate, and extends along a longitudinal axis 116. The base piece 106 includes a pair of opposed long edges 118, 119. A set of notches 120 is formed in the base piece 106. The notches 120 extend inwardly from the edge 118, in a direction that is generally transverse to the longitudinal axis 116. The notches 120 may provide the base piece 106 with flexibility (i.e. allow for the plate to flex).

In some embodiments, the notches 120 may not be needed on the side of the base piece 106 when the base piece 106 is made of material that is sufficiently flexible. The flexibility of the base piece 106 allows the first part 102 to be bent in either the transverse direction (with respect to the longitudinal axis of the first part 102) or in the vertical direction with respect to the bottom or top of the base piece 106. This flexibility allows the surgeon to place the first part 102 adjacent to a wound where the wound may not lie flat or may have a straight edges but may rather have curved edges that undulate vertically.

The width of the base piece 106 (i.e. the distance between the edges 118 and 119) may be selected to facilitate placement of sutures at a desired distance from an edge (i.e. fascial edge) of a wound, as will be described in further detail below. For example, the width of the base piece 106 may be selected so that the lumens of the needle portions are between about 2 mm and about 8 mm, or between about 4 mm and about 6 mm, or about 5 mm or about 7 mm away from the edge of the wound.

It should be noted that in an alternative embodiment, the width of one of the suture guide parts may be wider compared to the width of the other suture guide part. The suture guide part with the narrower width is then placed adjacent (i.e. proximal) to the wound while the suture guide part with the larger width is then placed distal with respect to the wound. The suture guide part having the larger width allows for better handling of the suture guide by the user. The larger width may be up to about three times the width of the base of the suture guide that is placed adjacent proximal to the wound.

As can be seen in FIGS. 6, and 9 to 10B, the second base piece 110 is of a similar configuration and flexibility compared to the first base piece 106, and for simplicity will not be described in detail.

Referring back to FIGS. 6 to 8B, as mentioned above, the first part 102 includes a plurality of needle portions 108. The needle portions 108 are joined to the base piece 106. As used herein, the term 'needle' refers to a substantially thin and cylindrical object, having a lumen extending longitudinally therethrough, and with a pointed end for piercing a tissue. The term 'needle portion' refers to any portion of such a needle.

Figure 8A:
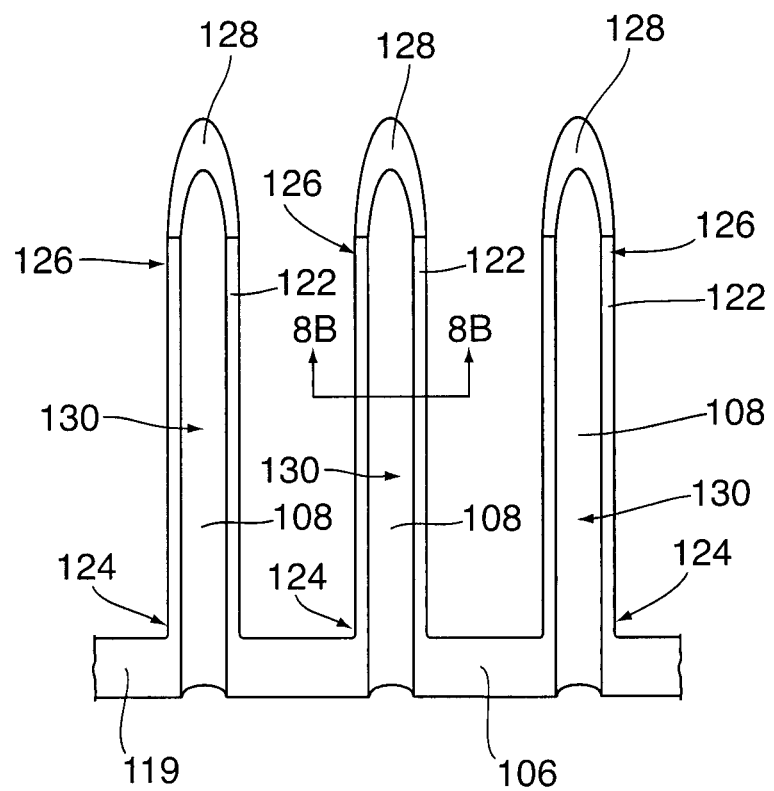
FIG. 8A is an enlarged side view of some of the needle portions of the first part of FIG. 7.
Figure 8B:
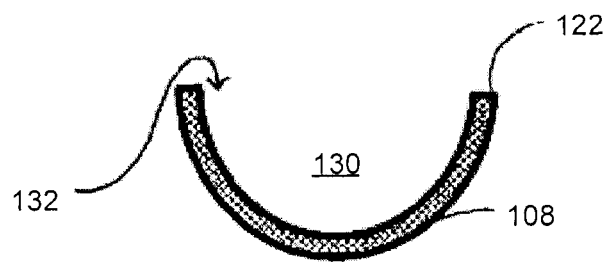
FIG. 8B is a cross section taken along line 8B-8B in FIG. 8A.

Referring to FIGS. 8A and 8B, in the example shown, the needle portions 108 of the first part are identical. Each needle portion 108 generally corresponds to a half of a needle, where the needle is halved along its longitudinal axis. Each needle portion 108 includes a needle portion sidewall 122, which in the example shown is generally semi-circular in transverse section. Each needle portion sidewall 122 has a proximal end 124 that is joined to the base piece 106, and an opposed distal end 126 that has a pointed tip 128. Each needle portion sidewall 122 defines a needle portion lumen 130, which extends between the proximal end 124 and the distal end 126, and provides a passage between the proximal end 124 and the distal end 126, both of which are open to the exterior environment. Furthermore, each needle portion sidewall 122 defines a longitudinally extending opening 132 (shown in FIG. 8B), which extends between the proximal end 124 and the distal end 126 of each respective needle portion 108, and is open to the needle portion lumen 130 and the exterior of the needle portion.

Figure 7:
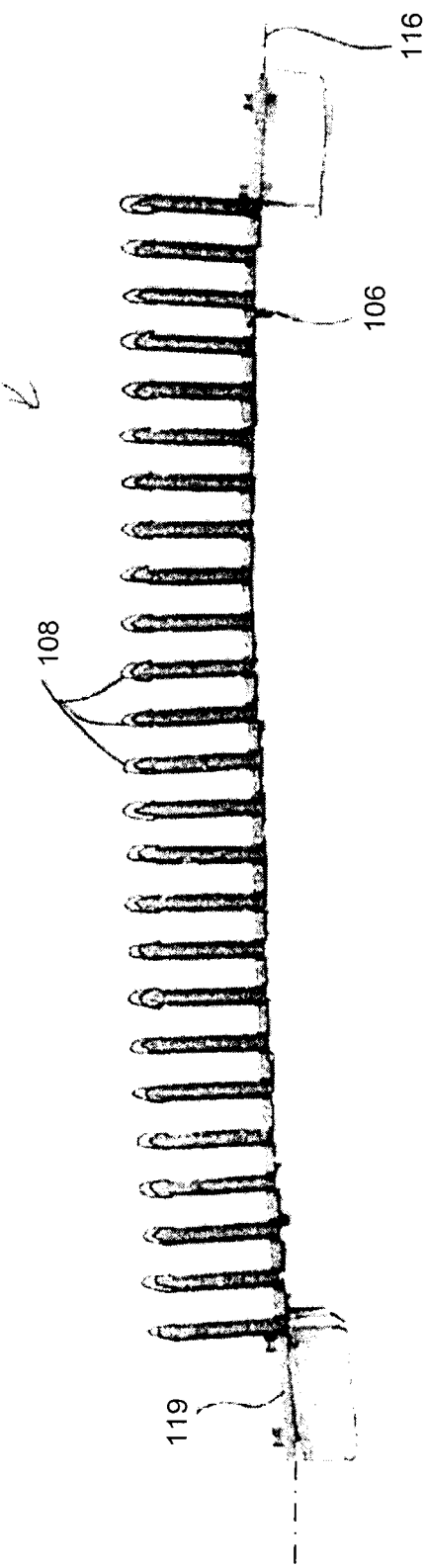
FIG. 7 is a side view of the first part of the suture guide of FIG. 6.

Referring to FIGS. 6 and 7, in the example shown, the needle portions 108 are arranged linearly along the edge 119 of the base piece 106, and nested into indentations in the base piece 106, with the openings 132 facing away from the base piece 106. In the example shown, the needle portions 108 are separately formed from the base piece 106, and are secured to the base piece 106 (e.g. by welding, adhesives, or mechanical fasteners). In other examples, the needle portions and the base piece can be integral.

Referring to FIGS. 6, and 9 to 10B in the example shown, the needle portions 112 of the second part 104 are of a similar configuration to the needle portions 108 of the first part 102. Briefly, as shown in FIGS. 10A and 10B, each needle portion 112 of the second part 104 includes a needle portion sidewall 134 that is semi-circular in transverse section, and that defines a needle portion lumen 136 and an opening 138. Each needle portion sidewall 134 extends between a respective proximal end 140 that is joined to the base piece 110, and a respective opposed distal end 142. In contrast to the distal ends 126 of the needle portions 108 of the first part 102, the distal ends 142 of the needle portions 112 of the second part 104 are not pointed. The remaining features of the needle portions 112 of the second part 104 are similar to the features of the needle portions 108 of the first part 102, and for simplicity will not be described in detail.

The distance (i.e. spacing) between successive needle portions moving longitudinally along the length of the suture guide parts 102 and 104 can be set in accordance with guidelines that are used for performing sutures for various types of wounds or operations such as, but not limited to, the European Hernia Society Guidelines for suturing incisions made during hernia operations, for example. For instance, the longitudinal spacing between the needle portions may be from about 3 to 5 mm. In an example embodiment, the longitudinal spacing between adjacent needle portions is about 5 mm.

In the example shown, the first part 102 and the second part 104 can be moved between a joined configuration (shown in FIGS. 1 to 5C) and a separated configuration (shown in FIG. 6).

Referring to FIG. 6, in the separated configuration, the first needle portions 108 are spaced away from the second needle portions 112.

Referring to FIGS. 5A to 5C, in the joined configuration, the first needle portions 108 are positioned adjacent the second needle portions 112. More specifically, each first needle portion 108 is positioned adjacent to and cooperates with a respective one of the second needle portions 112, to form a needle 144. Each needle 144 includes a respective needle sidewall that is formed by a respective one of the first needle portion sidewalls 122, and a respective one of the second needle portion sidewalls 134. Each needle 144 also includes a respective lumen (not shown), which is formed by one of the first needle portion lumens 130 and one of the second needle portion lumens 136, which join together. Each needle 144 also includes a respective pointed tip, which in the example shown is formed by a pointed tip 128 of a respective one of the first needle portions 108.

In the example shown, the first part 102 includes 25 needle portions, and the second part 104 includes 25 needle portions 112, which when in the joined configuration form 25 needles 144. In alternative examples, the suture guide may include another number of needle portions, which may form another number of needles, such as 2 needles, 4 needles, 6 needles, 8 needles, 10 needles, 14 needles, 20 needles or more than 25 needles.

In different embodiments, the needle portions of a first suture guide may be at a first height and the needle portions of a second suture guide may be at a second height where the first and second heights are different. For example, a suture guide with longer needles may be used when suturing thicker tissues. Alternatively, a suture guide with shorter needles may be used when suturing tissues where the working space is small (i.e. there are other organs or anatomical structures that are close by and using a suture guide with shorter needles will reduce the chances of accidentally puncturing an organ or other anatomical structure that should not be punctured.

In general the height of the needle portions is long enough to penetrate through all of the layers of tissue that are to be sutured. For example, for abdominal wounds, the height of the needle portions is such that all of layers of the abdominal wall can be sutured except for the skin. For example, the length of the needle portions may range from about 2 to 10 cm.

Figure 2:
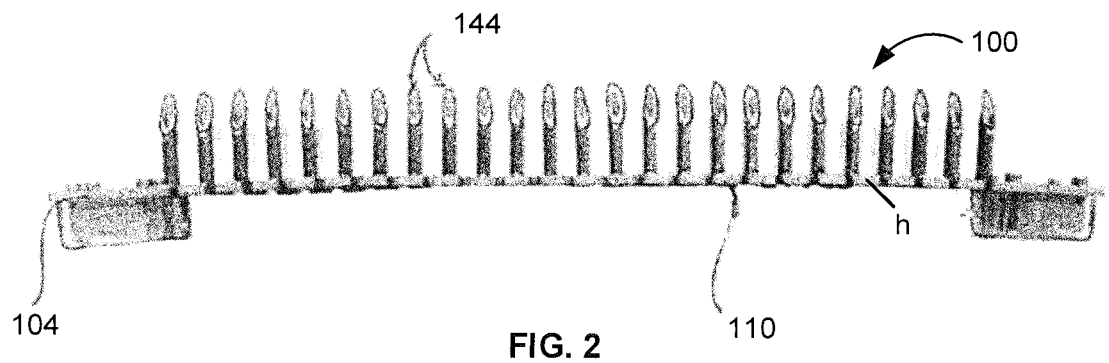
FIG. 2 is a side view of the suture guide of FIG. 1.

In some embodiments, different suture guides may have base pieces that have different heights h as shown for example in FIG. 2. Using a suture guide with a base having a particular height may help the user with handling the suture guide as a base having a larger height may be easier to manipulate including initial placement of the suture guide and then removal of the suture guide, as described in more detail below. For example, this height may range from about 2 to 3 cm in some embodiments.

In different embodiments, different suture guides may have different lengths and the user may select the suture guide that has a length that best matches the wound that is to be sutured. For example, the length of the suture guides may range from about 10 to 35 cm.

In different embodiments, the base pieces of the suture guides may be made of a material that provides sufficient rigidity and flexibility during use when suturing a wound but the material used for the base pieces may be soft enough so that it can be cut using a cutting tool, such as scissors or a knife, so that the length of the suture guides may be adjusted to match the length of the particular wound that is being sutured.

Referring to FIGS. 3 and 4, in the joined configuration, the first base piece 106 and second base piece 110 are positioned side-by-side, and longitudinal axes thereof are parallel.

Referring to FIG. 4, in the example shown, the first part 102 and second part 104 are removably securable in the joined configuration. More specifically, in the example shown, the first part 102 includes a set of first engagement members 146, which are mounted to the first base piece 106, and the second part 104 includes a set of second engagement members 148, which are mounted to the second base piece 110. The first engagement members 146 can clip to the second engagement members 148, respectively, to secure the first part 102 to the second part 104.

In alternative examples, the first part 102 and second part 104 can be removably secured in the joined configuration in another fashion, for example using a clamp that secures to both the first part 102 and the second part 104, or using a removable fastener such as a screw.

In the example shown, the first part 102 and second part 104 are completely separable from each other, as can be seen in FIG. 6. In alternative examples, when in the separated configuration, the first needle portions may be spaced away from the second needle portions, but other portions of the first part 102 and the second part 104 may remain joined together. For example, the first base piece 106 and the second base piece 110 may be joined together at one end by one or more hinges, so that the first base piece 106 and second base piece 110 can be pivoted away from each other to space the first needle portions away from the second needle portions.

The suture guide 100 may be fabricated from a variety of materials such as, but not limited to, metals, medical grade plastics or combinations thereof. For example, a metal may be used such as stainless steel, pure titanium or titanium-aluminum-vanadium. As another example, a medical grade hard plastic may be used such as PEEK (Poly Ether Ether Ketone). Alternatively, a composite material may be used including a combination of PEEK and stainless steel, carbon fibre or a combination of PEEK and carbon fibre. Any other applicable biocompatible materials having sufficient rigidity and flexibility may also be used. The particular material that is used is selected to provide sufficient rigidity and flexibility. Furthermore, the material used for the suture guide 100 may be sterilizable thereby allowing the suture guide 100 to be reusable, or the suture guide 100 may be designed for single use.

In some embodiments, the needle portions may be made of a harder material and the base pieces may be made of a softer, flexible material that still provides sufficient rigidity. It should be understood that in general the needle portions are made of material that is hard enough to penetrate through the different tissue layers that are to be sutured for wounds/incisions made at various locations of the patient's body.

A method for suturing a wound will now be described, with reference to FIGS. 11 to 17. The method will be described with reference to suture guide 100; however, the method may be carried out with other suture guides, and the suture guide 100 may be used according to other methods.

Figure 11:
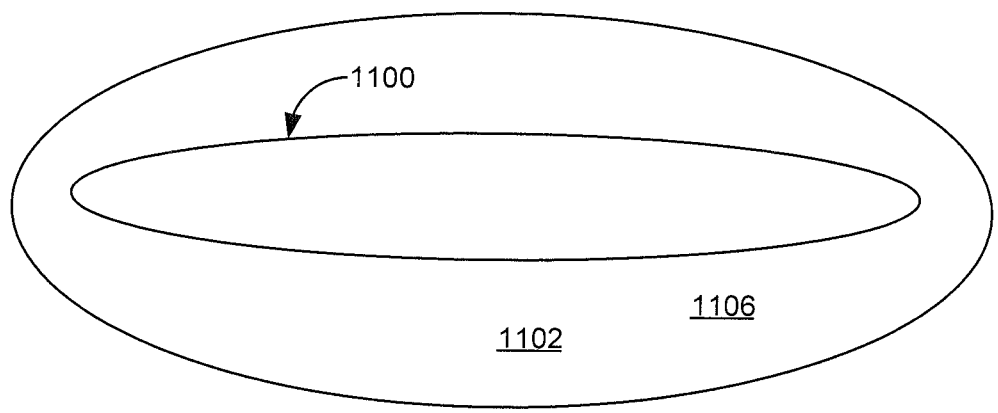
FIG. 11 is a schematic top view of a wound in an abdomen.

Referring to FIG. 11, a wound 1100 in a tissue is shown. In the example shown, the wound 1100 is a surgical incision in the abdomen 1102 of a patient, through the skin and subcutaneous tissue of the patient.

In the method shown, a pair of suture guides 100 as described above is used to suture the wound 1100. For clarity, the suture guides of the pair will be referred to as suture guide 100a and suture guide 100b, and reference numerals for the features of the suture guides 100a and 100b may be include the suffixes 'a' and 'b' respectively.

Figure 12:
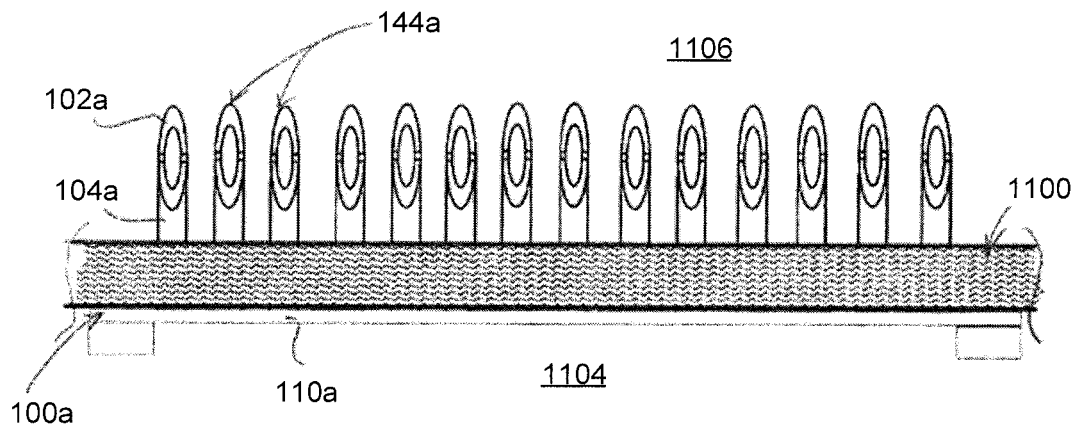
FIG. 12 is a side view of the suture guide of FIG. 1, with the needles thereof inserted through the tissue on a first side of the wound of FIG. 11.

Referring to FIG. 12, starting with the suture guide 100a, with the first part 102a and the second part 104a in the joined configuration, the needles 144a may be passed through the tissue on a first side of the wound 1100, along the length of the wound 1100. The needles 144a may be passed through the wound 1100 from the interior side 1104 of the tissue towards the exterior side 1106 of the tissue (e.g. into the subcutaneous tissue and out of the skin). In order to facilitate placement of the needles 144a, the edge of the base piece 110a may be aligned with the wound 1100 as the needles 144a are passed through the tissue, so that the needles 144a are positioned a distance D (shown in FIG. 13) from the wound 1100 that approximately corresponds to the width of the second base piece 110a. As stated above, the base pieces 106, 110 can have a width corresponding to an optimum distance for placement of a suture from a wound (e.g. 5 mm), in order to facilitate optimum placement of sutures.

The needles 144a can be passed through the tissue until the base pieces (only the second base piece 110a is visible in FIG. 12) contact the tissue.

Figure 13:
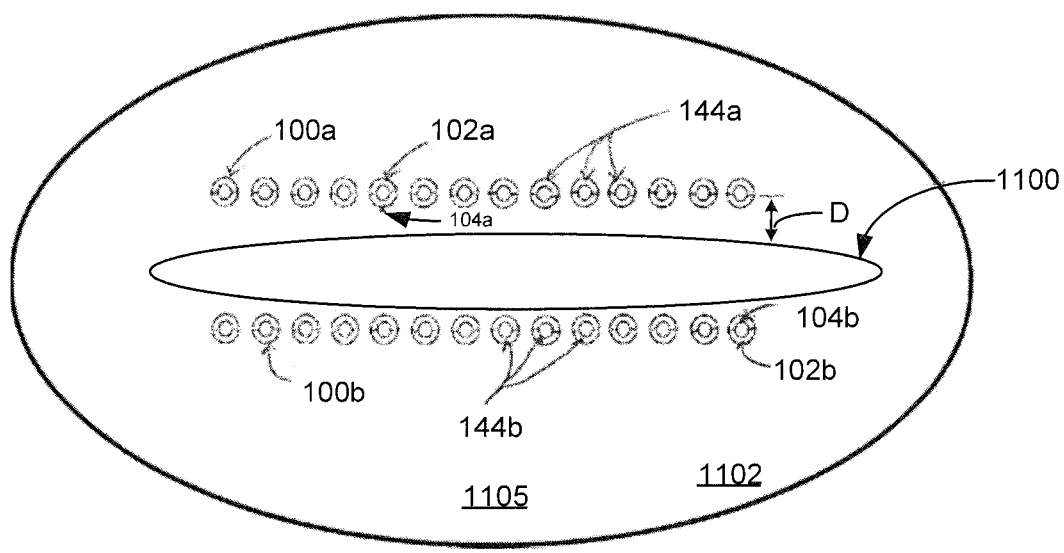
FIG. 13 is a schematic top view similar to that of FIG. 11, with a pair of the suture guides of FIG. 1 positioned on opposite sides of the wound, with the needles thereof inserted through the tissue.

Referring to FIG. 13, the suture guide 100b may be used in a similar fashion, on the second side of the wound. That is, with the first part 102b and the second part 104b in the joined configuration, the needles 144b may be passed through the tissue on the second side of the wound 1100, along the length of the wound. The needles 144b may be passed through the wound 1100 from the interior side 1104 of the tissue towards the exterior side 1106 of the tissue, and the edge of the base piece (not shown in FIG. 13) may be aligned with the wound as the needles 144b are passed through the tissue.

With the suture guides 100a and 100b in place, the wound 1100 may then be sutured via the suture guides 100a and 100b. In a first example, the wound may be sutured using one or more interrupted sutures. For example, referring to FIG. 14, a first portion 1108 of a suture 1110 may be passed through the tissue on the first side of the wound 1100, via one of the needles 144a of the suture guide 100a (referred to herein as a 'first needle'). The suture 1110 may be passed through the lumen of the first needle 144a (referred to as a 'first lumen'), from the proximal end to the distal end (or vice versa). A second portion 1112 of the suture 1110 may be passed through the tissue on the second side of the wound, via one of the needles 144b of the suture guide 100b (referred to herein as a 'second needle'). The second portion 1112 of the suture 1110 may be passed through the lumen of the second needle 144b (referred to as a 'second lumen'), from the proximal end to the distal end (or vice versa). This may be repeated with additional sutures, along the length of the wound 1100—e.g. another suture may be passed through the needle adjacent the first needle (i.e. a third needle), and through the needle adjacent the second needle (i.e. a fourth needle), and so on.

Alternatively, as shown in FIG. 15, the wound may be sutured using one or more continuous sutures (also known as running sutures), by lacing one long suture 1110 between the needles 144a of the first suture guide 100a and the needles 144b of the second suture guide 100b. Self-locking knots may be used with this suturing technique.

Figure 16:
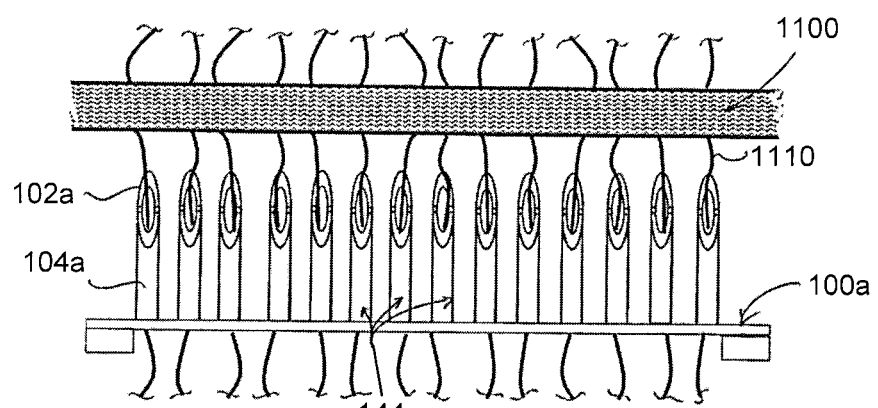
FIG. 16 is a side view similar to that of FIG. 12, showing the suture guide pulled away from the tissue, with the sutures still in place in the tissue.

Referring to FIG. 16, with the sutures 1110 in place (whether continuous or interrupted) and remaining relatively loose, the suture guide 100a may be pulled back from the tissue on the first side of the wound 1100, to remove the needles 144a from the tissue on the first side of the wound 1100, while maintaining the sutures 1110 in the tissue. This may be repeated with the second suture guide 100b (the removal of needles 144b of the second suture guide is not shown).

Figure 17:
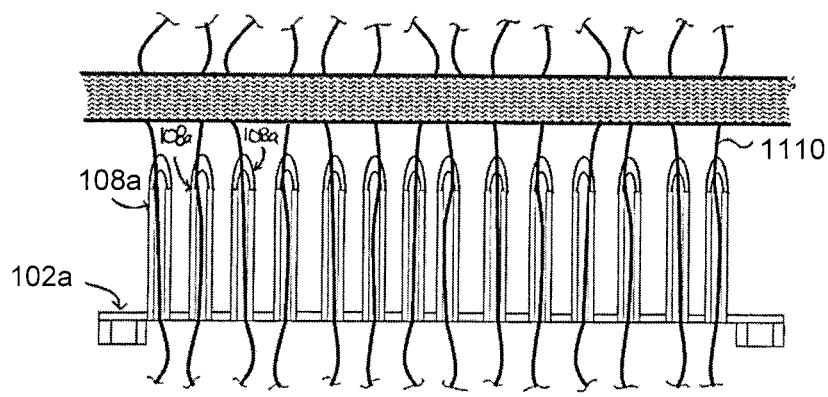
FIG. 17 is a side view similar to that of FIG. 16, after separation of the second part of the suture guide from the first part of the suture guide.

The needles 144a of the suture guide 100a may then be separated from the sutures 1110, by moving the first part 102a and the second part 104a of the suture guide 100a to the separated configuration. Referring to FIG. 17, the second part 104a (not shown in FIG. 17) has been removed from the first part 102a, so that the first part 102a and second part 104a are in the separated configuration. When the first part 102a and the second part 104a are in the separated configuration, the needle portions 108a of the first part 102a are spaced away from the needle portions 112a of the second part 104a (not shown in FIG. 17), and the first part 102a and the second part 104a can be removed from the sutures 1110 and from the patient. This may be repeated with the second suture guide 100b, by moving the first part 102a and the second part 102b to the separated configuration (not shown), to separate the needles 144b of the suture guide 100b from the sutures 1110.

When the suture guides 100a, 100b have been removed from the sutures 1110, the sutures can be tightened, and tied off (not shown), for example by tying the first portion of the suture to the second portion of the suture.

The suture guides described herein can be used with a number 1 or a number 2 absorbable monofilament suture material. The suture guides described herein are generally compatible with any type of conventional suture material currently used in medical settings.

It should be noted that in some cases, definitive closure of the wound can be postponed with the sutures in place, by delaying the traction on the suture material that is used.

In some examples, the suture guide described herein may be provided in a kit with one or more tools for aiding in pressing the needle portions 108, 112 through a tissue.

Figure 18:
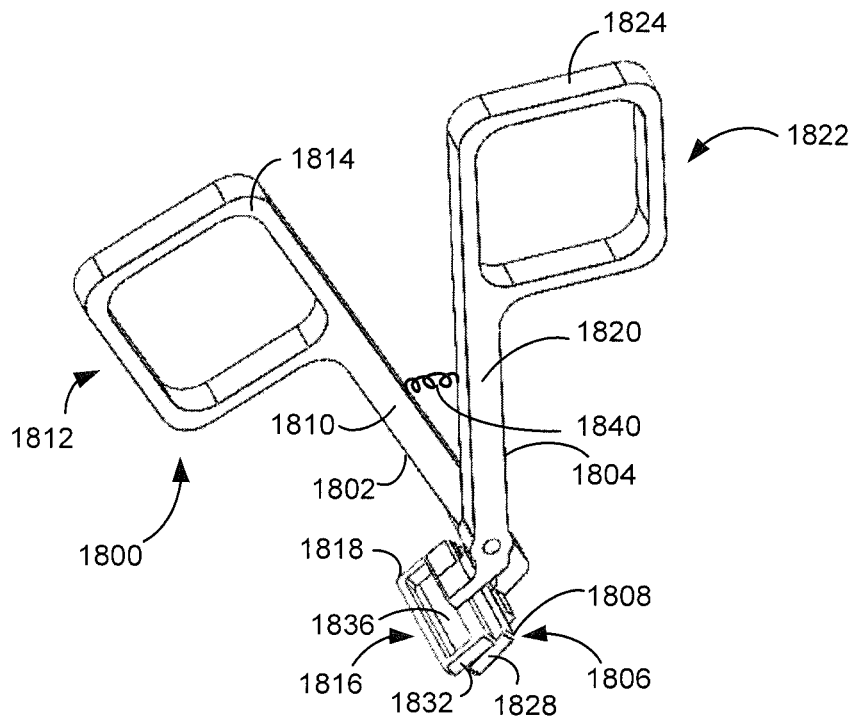
FIG. 18 is a perspective view of an example clamp tool for pressing needle portions of a suture guide through a tissue.
Figure 19:
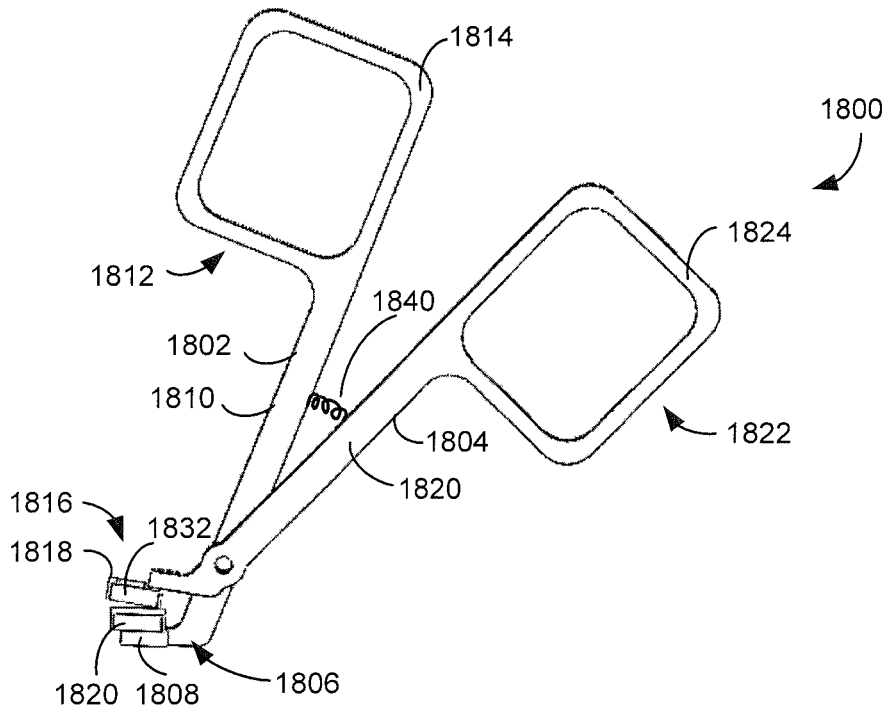
FIG. 19 is a side view of the clamp tool of FIG. 18.

Referring now to FIGS. 18 and 19, an example tool 1800 is shown. The tool 1800 includes a first arm 1802 and a second arm 1804. The first arm 1802 includes a first arm distal end 1806 with a first arm end effector 1808, a first arm middle portion 1810, and a first arm proximal end 1812 with a first arm grasping member 1814. Similarly the second arm 1804 includes a second arm distal end 1816 with a second arm end effector 1818, a second arm middle portion 1820 and a second arm proximal end 1822 with second arm grasping member 1824.

In the example shown, the first arm middle portion 1810 and second arm middle portion 1820 are rotatably mounted together about a rotation axis 1826 (shown in FIG. 22), such that movement of the first arm grasping member 1814 towards the second arm grasping member 1824 effects movement of the first arm end effector 1808 towards the second arm end effector 1818.

In the example shown, the first arm grasping member 1814 and second arm grasping member 1824 are each in the form of a loop, through which a user's fingers may be inserted. Flexing and extending of the user's fingers may effect movement of the first arm grasping member 1814 towards and away from second arm grasping member 1824.

Figure 20:
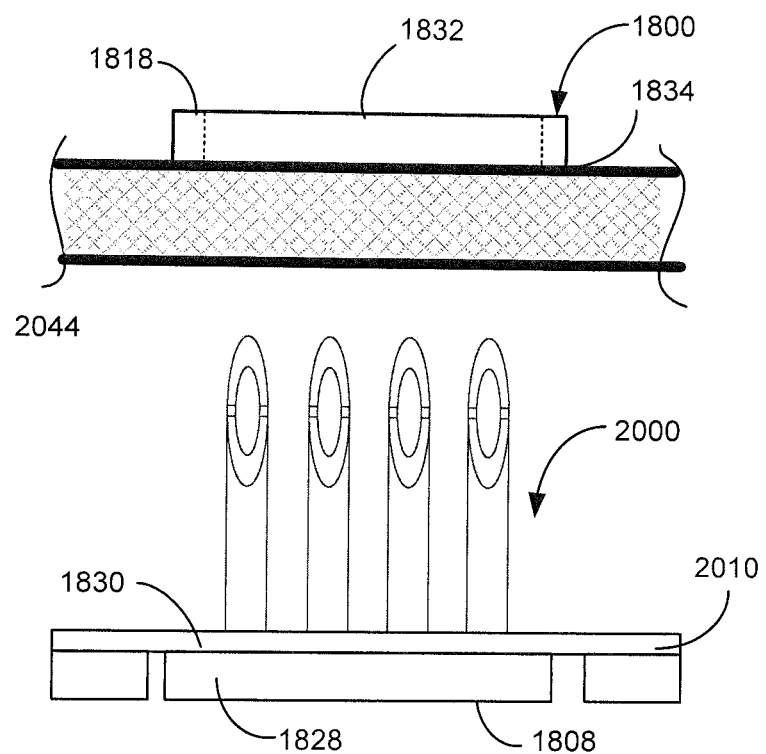
FIG. 20 is a schematic end view showing the end effectors of the clamp tool of FIG. 19 in position to press the needle portions of a suture guide through a tissue.
Figure 21:
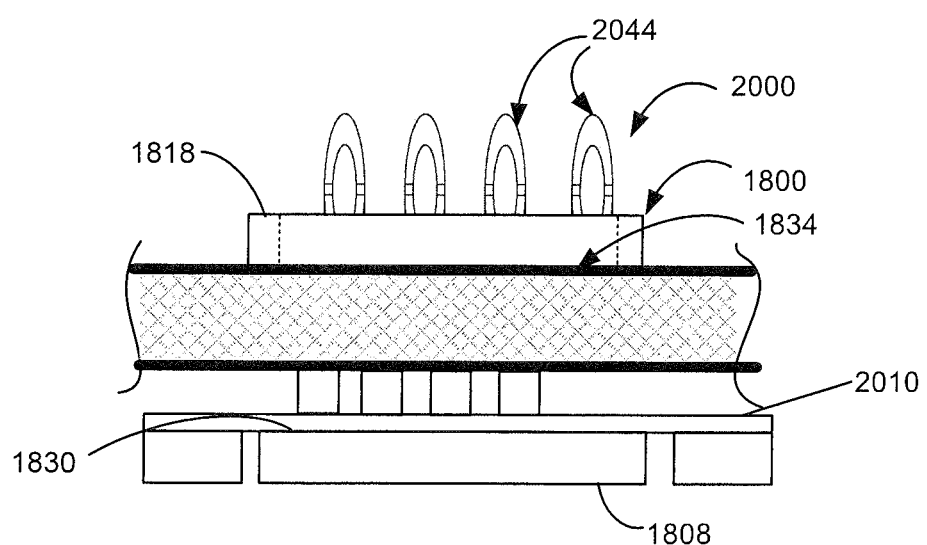
FIG. 21 is a schematic end view similar to that of FIG. 20, showing the end effectors pressing the needle portions through the tissue.

In the example shown, the first arm end effector 1808 includes a first plate 1828, which defines a first abutment surface 1830 (shown in FIGS. 20 and 21). The first abutment surface 1830 is generally parallel to the rotation axis 1826. In use, the first abutment surface 1830 can abut one or both of the base pieces of a suture guide.

In the example shown, the second arm end effector 1818 includes a second plate 1832, which defines a second abutment surface 1834 (shown in FIGS. 20 and 21). The second abutment surface 1834 is generally parallel to the rotation axis 1826. The second plate 1832 has an opening 1836 extending therethrough, for passage of one, some, or all of the needle portions of a suture guide.

In the example shown, the tool 1800 further comprises a spring 1840 that is coupled between a portion of the first arm 1802 and a portion of the second arm 1804 such as the mid-portions 1810 and 1820, respectively. The spring 1840 functions to maintain the end effectors 1816 and 1818 spaced apart from one another in an open position when the tool 1800 is not in use. Therefore, the user has to apply a compressive force to the grasping members 1814 and 1824 to move the end effectors 1816 and 1818 towards each other. In the example embodiment, the spring 1840 is a compression spring but it should be understood that other types of springs may be used such as, but not limited to, a cantilever spring, a leaf spring or a bow spring, for example. The spring 1840 may be made of metal or another suitable material.

Figure 22:
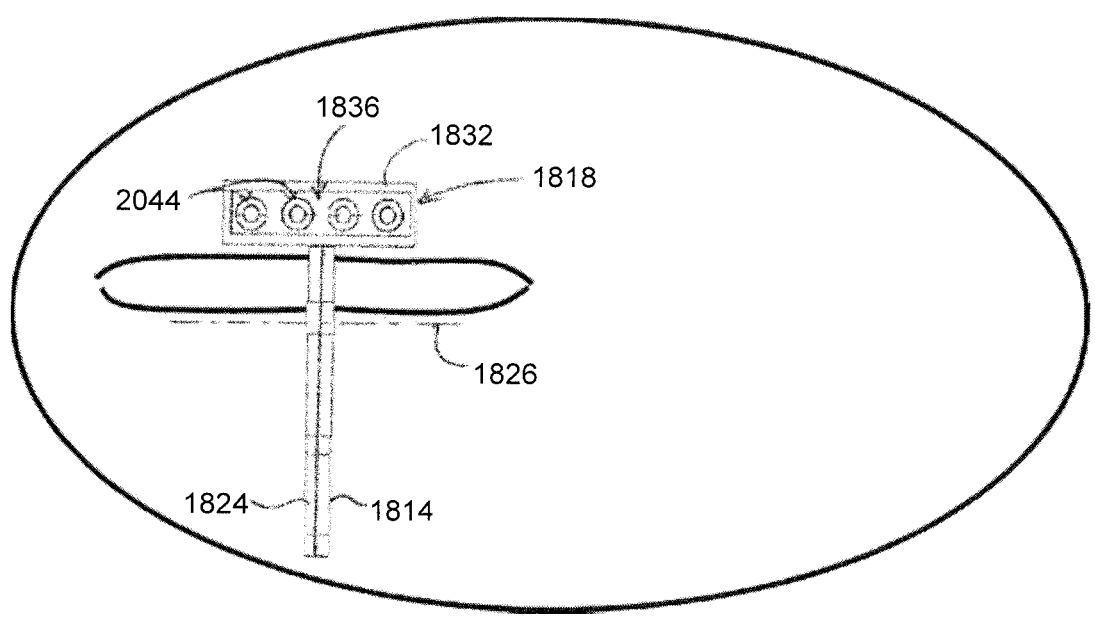
FIG. 22 is a schematic top view of a wound in an abdomen, after the clamp tool of FIG. 19 has pressed the needle portions through the tissue adjacent the wound.

An example use of the tool 1800 will be described with reference to FIGS. 20 to 22. In FIGS. 20 to 22, the tool 1800 is shown being used with an alternative suture guide 2000, which is similar to suture guide 100, but has only four needles 2044. Furthermore, for simplicity, only the end effectors 1808, 1818 of the tool 1800 are shown in FIGS. 20 and 21.

Referring to FIG. 20, in use, the tool 1800 may be positioned so that the first arm end effector 1808 is on an interior side of a wound, abutting the base pieces (only the second base piece 2010 is shown) of the suture guide 2000, and so that the second arm end effector 1818 is on an exterior side of the wound, abutting the tissue adjacent the wound The grasping members 1814, 1824 may be squeezed towards each other. Referring to FIGS. 20 and 21, this forces the first arm end effector 1808 and second arm end effector 1818 towards each other, to press the needles 2044 of the suture guide 2000 into the tissue. When the needles 2044 begin to poke through the tissue, they may pass into the opening 1836 in the second arm end effector 1818, and squeezing may be continued, until the base pieces of the suture guide 2000 contact the tissue. The tool 1800 may then be removed from the patient.

In some examples, the suture guides described herein may also be provided in a kit with one or more needle guards, which may be used to minimize the risk of needle stick injuries while sutures are being inserted into the needles of the suture guide.

Referring to FIGS. 23 and 24, front and side views of an example needle guard 2300 are shown. The needle guard 2300 includes an elongate body 2302, having a first end 2304 and an opposed second end 2306. The first end 2304 is flared. A passage 2307 (shown in dotted line) extends through the body 2302. The passage 2307 has a first portion in the first end 2306, and a second portion in the second end 2304. The length of the first portion of the passage 2307 is approximately equal to the length of the needles 144. The second portion of the passage 2307 is flared.

The use of the needle guard 2300 will be described with reference to FIG. 25. For simplicity, the use of one needle guard 2300 will be described with reference to one needle 144 of the suture guide 100. However, a plurality of needle guards 2300 may be used with a plurality of the needles 144. In such cases, the needle guards may be separately formed, or formed together as one piece.

Referring to FIG. 25, in use, after the needle 144 of the suture guide 100 has been pressed through a tissue, the needle guard 2300 may be placed on to the needle 144, so that the needle 144 is inside the passage 2307, with the pointed tip 128 nested in the first portion of the passage. With the pointed tip 128 of the needle 144 in this position, the user is protected from needle stick injuries. When the user is ready to start applying the suture the needle guards are removed before the suture is passed through the needle portions.

In an alternative embodiment, the needle guards may have be made of two separate needle guard portions that have engagement portions that allow separate needle guard portions to be removably attachable with one another. For instance, one needle guard portion may have one or more pins extending horizontally away from its main body and the other needle guard portion may have a corresponding channel or groove in its main body for removably receiving the pin to allow the needle guard portions to be attached and detached from one another. Alternatively, the main body of one needle guard portion may include a clip portion and the main body of another needle guard portion may include a rib or post that is removably engaged by the clip portion allowing the needle guard portions to be attached and detached from one another. Therefore, for a given needle guard, the two portions of the needle guard may be attached to one another to form a needle guard as shown in FIGS. 23-25, the given needle guard may then be placed on a needle portion of the suture guide and after the suture material is inserted through the needle portion (or after the suture is inserted through all needle portions of the suture guide), the given needle guard may be removed by separating the needle guard portions from one another (as was described for removing the suture guide parts from one another).

In an alternative embodiment, separate needle guards may be connected to one another to form one single piece that can be applied to the suture guide such that each needle guard engages a corresponding needle portion. For example, ribs or strips can be used to connect the exterior of the main body portions of adjacent needle guards to one another. This allows all of the needle portions to be covered at the same time. This is in contrast to using physically separate needle guards where the needle guards are applied to the needle portions one by one, which is more time consuming and there is an increased risk of someone dropping one of the needle guards either on the floor which requires re-sterilization or inside the patient.

Figure 26A:
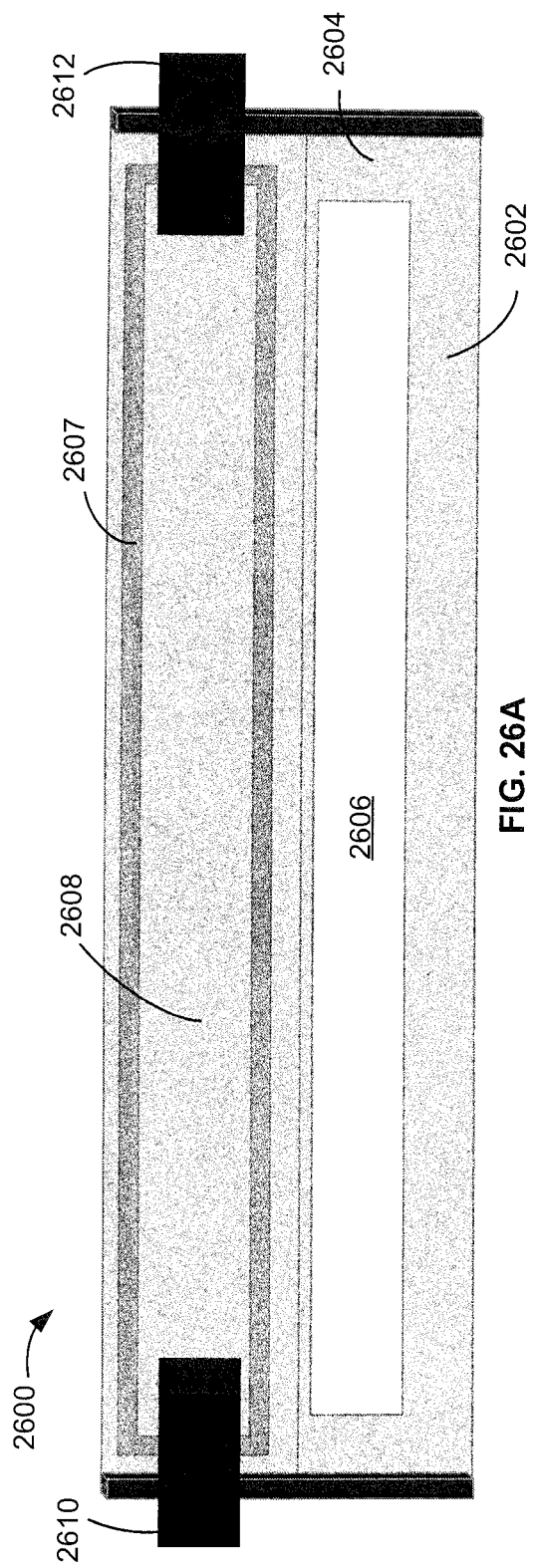
FIGS. 26A and 26B are top views of an example embodiment of a removable handle attachment alone and attached to a suture guide, respectively, in accordance with the teachings herein.
Figure 26B:
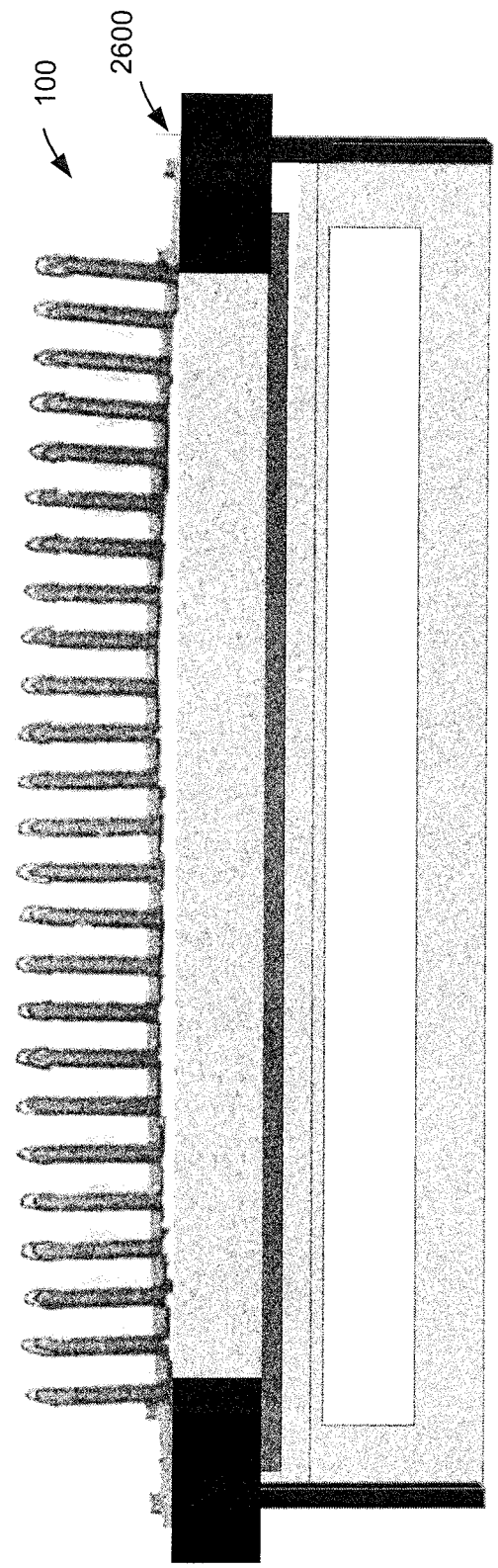

Referring now to FIGS. 26A and 26B, FIG. 26A is a top view of an example embodiment of a handle attachment 2600 that may be used with any of the suture guides described herein and FIG. 26B shows the handle attachment 2600 attached to the suture guide 100. The handle attachment 2600 allows the user (i.e. surgeon) to more easily manipulate and place the suture guide 100 at a desired location where sutures are to be applied, such as adjacent to the wound that is to be sutured. The user can then use the handle attachment 2600 to hold onto the suture guide 100 with one hand as the user then uses their other hand to manipulate the tool 1800 to push the needle portions of the suture guide 100 through the tissue adjacent to the wound where the suture is to be applied. Accordingly, the user can use the tool 1800 as was previously described.

The handle attachment 2600 comprises a handle 2602 that is spaced apart from a main body 2604 thereby creating an aperture 2606 that the user's fingers may go through as they grasp the handle 2602. The handle attachment 2600 also comprises a base 2608 for receiving the suture guide 100. The base 2608 is sized to be larger than the suture guide 100 and may be recessed. The handle attachment 2600 also comprises retaining members 2610 and 2612 to hold the suture guide 100 in place. The handle attachment 2600 may also optionally include a flange or raised edge 2607 which can also be used to line up the suture guide 100 when it is placed on the base 2608. Once the suture guide 100 is placed on the base 2608, the retaining members 2610 and 2612, which may be clamps as shown in this example, can be applied to either longitudinal end of the suture guide 100, as shown in FIG. 26B, to releasably attach the handle attachment 2600 to the suture guide 100. For example, the clamps can be depressed, the suture guide 100 can be placed on the base 2608 and then the clamps can be released to engage the longitudinal ends of the suture guide 100 and hold the suture guide 100 in place on the base 2608 of the attachment handle 2060. When the handle attachment 2600 is no longer needed, the clamps can be depressed so that they move away from the ends of the suture guide allowing the handle attachment to be removed from the suture guide. In other embodiments, other types of retaining members may be used that can secure the suture guide to the handle attachment 2600.

For example, in an alternative embodiment the retaining members 2610 and 2612 may be sliding tabs that can slide through slots (not shown) that are in the sides of the handle attachment such that the tabs are oriented parallel or transverse to the longitudinal axis of the suture guide. After the suture guide 100 has been placed on the base 2608, the tabs can be slid over the surface of the ends of the suture guide 100 that are facing away from the handle attachment 2600 to secure the suture guide 100 to the handle attachment 2600. When the handle attachment 2600 is no longer needed, the tabs can then be slid back out so that handle attachment 2600 can be removed from the suture guide 100.

Alternatively, the retaining members 2610 and 2612 may be tabs that are pivotally attached to the attachment handle 2600 with a pivot points at the opposite ends of attachment handle 2600. The pivot tabs can be rotated away from the base 2608 so that the suture guide 100 can be placed on the base 2608. After the suture guide 100 has been placed on the base 2608, the pivot tabs can be pivoted so that they cover the surface of the ends of the suture guide 100 that are facing away from the handle attachment 2600 to secure the suture guide 100 to the handle attachment 2600. When the handle attachment 2600 is no longer needed, the pivot tabs can then be pivoted away from the suture guide 100 so that handle attachment 2600 can be removed from the suture guide 100.

It should be noted that a kit, in accordance with the teachings herein, was used by the inventor to apply sutures on an abdominal incision made on a pig that was anesthetized. The test indicated that the kit allowed for the speed and precision of the suturing to be increased compared to conventional techniques of applying sutures. For example, the time to apply the sutures using the kit was approximately 6 minutes. This is in contrast to times of about 35 min for applying sutures using a conventional needle in the inventor's experience.

During this test, the fascia was grasped using four clamps such as Kocher clamps. Two of the clamps were used to grasp the fascial edges of the wound (i.e. incision), one on each side of the vertex of the incision. The other two clamps were placed at the bottom of the incision in a similar fashion. Initially, the fascial edge located on the left side of the animal was pulled medially by applying traction to the previously positioned pair of Kocher clamps. Once the fascial edge was pulled to the midline, one of the suture guides was inserted underneath that edge. The needle portions of the suture guide were pointing upwards resting against the parietal peritoneum directly underneath the area previously marked to receive the needle bites. Subsequently, the tool was used to compress the fascia against the needle portions until full thickness perforations were obtained along the fascial edge. The same procedure was performed on the fascial edge located on the opposite side of the incision using a second suture guide. Once the suture guides were securely applied to each side to the fascia, a 1-0 polydioxanone monofilament suture (PDS II, Ethicon Inc., Somerville, N.J.), without a needle, was manually passed through each one of the needle portions of the suture guides. A hemostat was placed on the distal end of the suture. The initial pass was from outside-in through the uppermost needle portion of the suture guide placed on the left side of the incision. The second pass was from the inside-out through the uppermost needle portion of the suture guide placed on the right side of the fascial incision. This process was repeated in succession until the final pass on the last needle portions. At this point, the suture guides were removed from each side of the fascial incision. The suture was then tied and square knots were applied. Subsequently, the suture was pulled distally until taut and several additional square knots were applied at the end of the incision.

From anecdotal testing, it can be seen that the suture guides of the present teachings allow for shorter closure times when suturing a wound, which may reduce the chances of tissue necrosis during suturing. In addition, the suture guides of the present teachings allow for a controlled and even traction on the suture, thereby avoiding excessive pressure thereby avoiding unnecessary damage to the fascial edges and necrosis of the tissue at the suture site.

Furthermore, the suture guides described in accordance with the teachings herein allows sutures to be applied without having to place a needle on the end of the suture for stitching up a wound as is done conventionally. This is safer for the patient since it reduces the chance of a surgeon puncturing any organs or anatomy of the patient that are near the wound/incision when the surgeon is applying the suture. For example, when suturing an abdominal wound the suture guide decreases the chances of inadvertent bowel perforation.

In one aspect, in accordance with the teachings herein, in at least one embodiment a kit is provided which includes more than one pair of suture guides, the tool 1800, optionally the needle guards 2300 and optionally the handle attachment 2600, where each pair of suture guides is of different length and the user may select the pair of suture guides having the length that best matches the length of the wound that is to be sutured. Alternatively each suture guide in the kit may have different lengths if the user is only interested in using one suture guide.

In another aspect, in accordance with the teachings herein, in at least one embodiment a kit is provided which includes more than one pair of suture guides, the tool 1800, optionally the needle guards 2300 and optionally the handle attachment 2600, where a first pair of the suture guides has needles having a first height, the second pair of the suture guides has needles having a second height, and so on. During use, the user selects the pair of suture guides with needles having a height that is suitable for use with the particular tissue that is to be sutured since different tissues at different anatomical locations or for different patients (e.g. for different humans and/or different animals) may have different thicknesses. Alternatively each suture guide in the kit may have needle portions of different heights if the user is only interested in using one suture guide.

In yet another aspect, in accordance with the teachings herein, in at least one embodiment a kit is provided which includes more than one pair of suture guides, the tool 1800, optionally the needle guards 2300 and optionally the handle attachment 2600, where a first pair of the suture guides has needles having a first wall thickness, the second pair of the suture guides has needles having a second wall thickness, and so on. Different wall thickness for the needle portions can provide different stiffness and flexibility, which may be useful from a tactile perspective or when the tissue being sutured has a different thickness and therefore a different needle diameter may be more appropriate. Alternatively, or in addition thereto, there may also be different suture guides that have different diameters for the needle portions. For example, different diameters can be used that correspond to the nomenclature for different sutures (e.g. 2-0, 3-0, etc.). During use, the user selects the pair of suture guides with needles having an appropriate diameter and/or thickness for use with the particular tissue that is to be sutured since different tissues at different anatomical locations or for different patients (e.g. for different humans and/or different animals) may have different thicknesses. Alternatively each suture guide in the kit may have needle portions of different diameters and/or thicknesses if the user is only interested in using one suture guide.

While the above description provides examples of one or more processes or apparatuses, it will be appreciated that other processes or apparatuses may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

The invention claimed is:

1. A suture guide comprising:
   first suture guide part having a first base piece and a plurality of first needle portions joined to the first base piece, each first needle portion having a respective first needle portion sidewall; and
   a second suture guide part having a second base piece and a plurality of second needle portions joined to the second base piece, each second needle portion having a respective second needle portion sidewall;
   wherein the first suture guide part and second suture guide part are moveable between a separated configuration and a joined configuration;
   wherein in the separated configuration, the plurality of first needle portions are spaced away from the plurality of second needle portions; and
   wherein in the joined configuration, each one of the first needle portions is positioned adjacent and cooperates with a respective one of the second needle portions to form a needle, each needle having a respective needle sidewall formed by one of the first needle portion sidewalls and one of the second needle portion sidewalls, and each needle sidewall defining, respectively, a lumen and a pointed tip.

2. The suture guide of claim 1, wherein:
   each first needle portion sidewall defines a respective first needle portion lumen and has a respective first proximal end joined to the first base piece, and a respective opposed first distal end, and
   each second needle portion sidewall defines a respective second needle portion lumen and has a respective second proximal end joined to the second base piece, and a respective opposed second distal end.

3. The suture guide of claim 2, wherein
   each first needle portion sidewall defines a respective first opening extending between the first proximal end thereof and the first distal end thereof, and
   each second needle portion sidewall defines a respective second opening extending between the second proximal end thereof and the second distal end thereof.

4. The suture guide of claim 2, wherein when the first suture guide part and the second suture guide part are in the joined configuration, each one of the first needle portion lumens joins with a respective one of the second needle portion lumens to form a respective one of the lumens.

5. The suture guide of claim 1, wherein
   the plurality of first needle portions are arranged linearly along an edge of the first base piece with each first opening facing away from the first base piece, and
   the plurality of second needle portions are arranged linearly along an edge of the second base piece with each second opening facing away from the second base piece.

6. The suture guide of claim 1, wherein the first suture guide part comprises a first engagement member, the second suture guide part comprises a second engagement member, and the first engagement member is releasably securable to the second engagement member to maintain the first suture guide part and the second suture guide part in the joined configuration.

7. The suture guide of claim 1, wherein
   the first base piece comprises a first elongate plate and extends along a first longitudinal axis, and the second base piece comprises a second elongate plate and extends along a second longitudinal axis; and
   when the first suture guide part and the second suture guide part are in the joined configuration, the first base piece and second base piece are positioned side-by-side and the first longitudinal axis and second longitudinal axis are parallel.

8. The suture guide of claim 7, wherein the first base piece comprises a set of notches therein, and the set of notches extend transverse to the first longitudinal axis.

9. The suture guide of claim 1, wherein when in a transverse section, each first needle portion sidewall and each second needle portion sidewall is semicircular.

* * * * *